(12) United States Patent
Margraf et al.

(10) Patent No.: US 10,054,484 B2
(45) Date of Patent: Aug. 21, 2018

(54) MEASURING ARRANGEMENT FOR REFLECTION MEASUREMENT

(71) Applicant: Carl Zeiss Spectroscopy GmgH, Jena (DE)

(72) Inventors: Jörg Margraf, Königsee-Rottenbach (DE); Jens Mondry, Jena (DE)

(73) Assignee: CARL ZEISS SPECTROSCOPY GMBH, Jena (DE)

( * ) Notice: Subject to any disclaimer, the term of this patent is extended or adjusted under 35 U.S.C. 154(b) by 0 days.

(21) Appl. No.: 15/328,523

(22) PCT Filed: Jun. 22, 2015

(86) PCT No.: PCT/EP2015/063898
§ 371 (c)(1),
(2) Date: Jan. 24, 2017

(87) PCT Pub. No.: WO2016/015921
PCT Pub. Date: Feb. 4, 2016

(65) Prior Publication Data
US 2017/0211975 A1    Jul. 27, 2017

(30) Foreign Application Priority Data

Aug. 1, 2014   (DE) .................. 10 2014 215 193

(51) Int. Cl.
*G01N 21/55* (2014.01)
*G01J 3/02* (2006.01)
(Continued)

(52) U.S. Cl.
CPC ............. *G01J 3/0251* (2013.01); *G01J 3/021* (2013.01); *G01J 3/50* (2013.01); *G01N 21/27* (2013.01);
(Continued)

(58) Field of Classification Search
CPC .... G02B 1/04; G02B 27/0172; G02B 5/3083; G02B 6/0046; G02B 2027/0178;
(Continued)

(56) References Cited

U.S. PATENT DOCUMENTS

| 3,874,799 A | 4/1975 | Isaacs et al. |
| 4,881,811 A | 11/1989 | O'Brien |

(Continued)

FOREIGN PATENT DOCUMENTS

| DE | 19528855 | 2/1997 |
| DE | 10010213 | 9/2001 |
| EP | 2 267 420 | 12/2010 |

OTHER PUBLICATIONS

International Search Report for PCT/EP2015/063898 dated Sep. 29, 2015.

*Primary Examiner* — Michael P Stafira
(74) *Attorney, Agent, or Firm* — Nixon Peabody LLP; Jeffrey L. Costellia

(57) ABSTRACT

The invention relates to a measuring arrangement for detecting an absolute reflection spectrum of a sample in a process for producing the sample. It comprises a light source for generating measurement light, a homogenizer for generating a uniform spatial illuminance distribution of the measurement light; a movable reflector and a receiver for collecting the measurement light reflected from the sample and/or the reflector. According to the invention, the reflector both for a reference measurement and for a sample measurement is positioned in an observation beam path and arranged on the same side of the sample as the light source in order to feed the reflected measurement light to the receiver.

11 Claims, 4 Drawing Sheets

Figure 5:
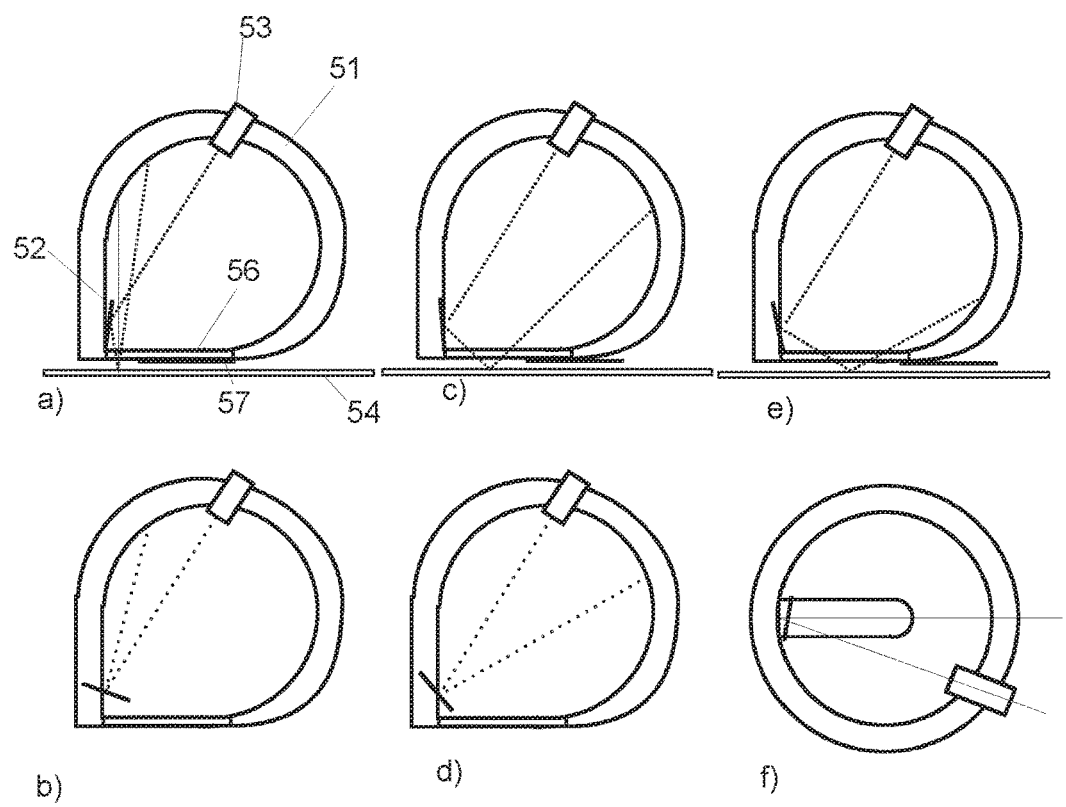

(51) Int. Cl.
    *G01N 21/47*     (2006.01)
    *G01N 21/27*     (2006.01)
    *G01N 21/86*     (2006.01)
    *G01J 3/50*      (2006.01)

(52) U.S. Cl.
    CPC .......... *G01N 21/474* (2013.01); *G01N 21/86* (2013.01); *G01N 2021/4754* (2013.01); *G01N 2021/8618* (2013.01); *G01N 2201/065* (2013.01)

(58) Field of Classification Search
    CPC .. G02B 27/017; G02B 27/141; G02B 6/0053; G02B 6/0055; G02B 2027/0138; G02B 2027/0187; G02B 26/008; G02B 27/0955; G02B 27/30
    See application file for complete search history.

(56) References Cited

U.S. PATENT DOCUMENTS

| | | | | |
|---|---|---|---|---|
| 6,229,614 B1* | 5/2001 | Larsen | .................... | G01J 3/453 356/451 |
| 2003/0023152 A1* | 1/2003 | Abbink | ................ | A61B 5/0075 600/316 |

* cited by examiner

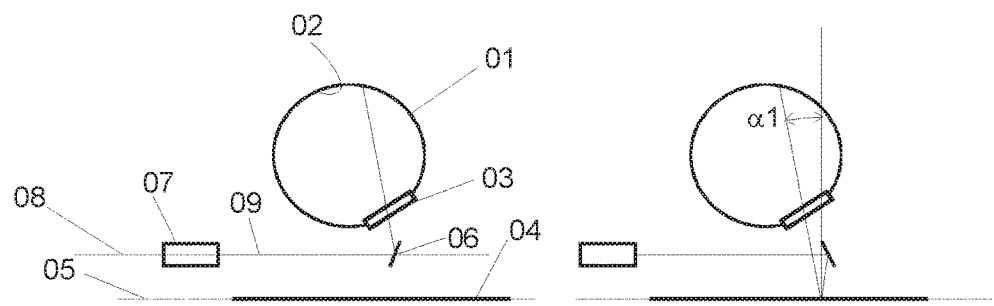
Fig. 1 a) b)
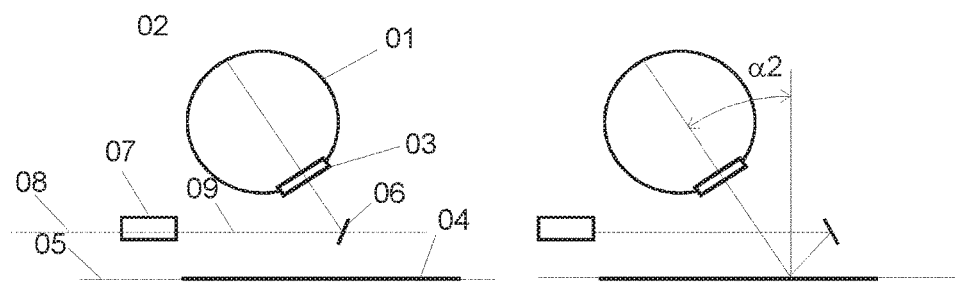
Fig. 2 a) b)
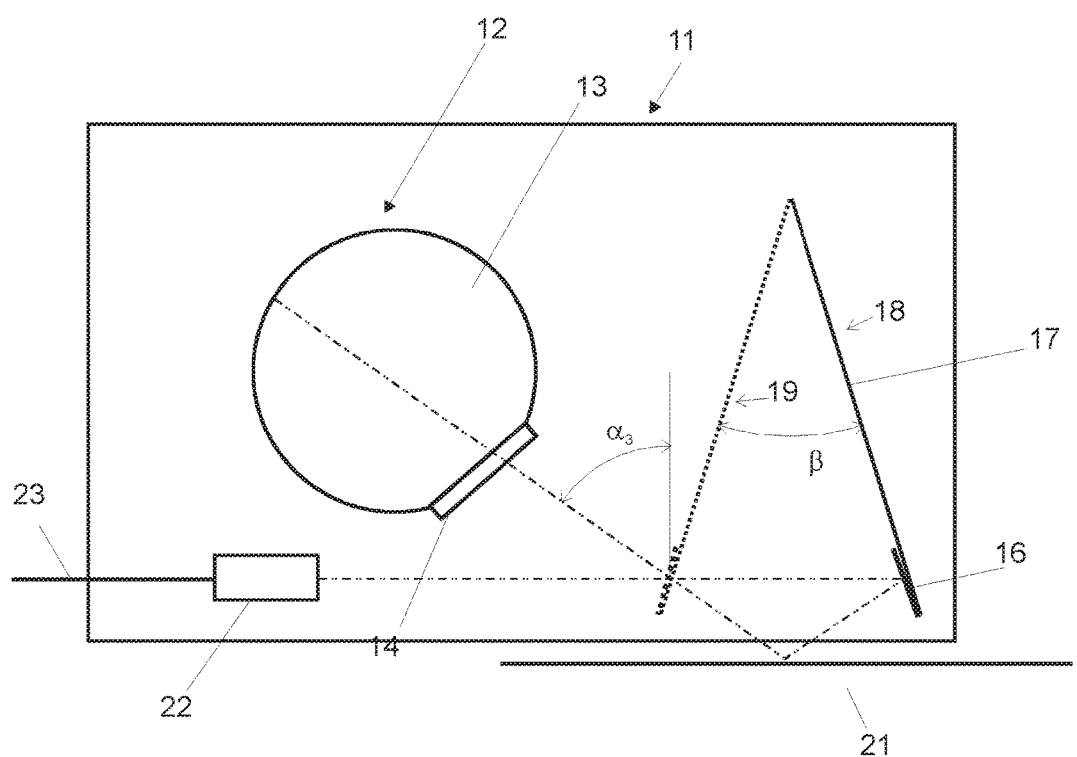
Fig. 3

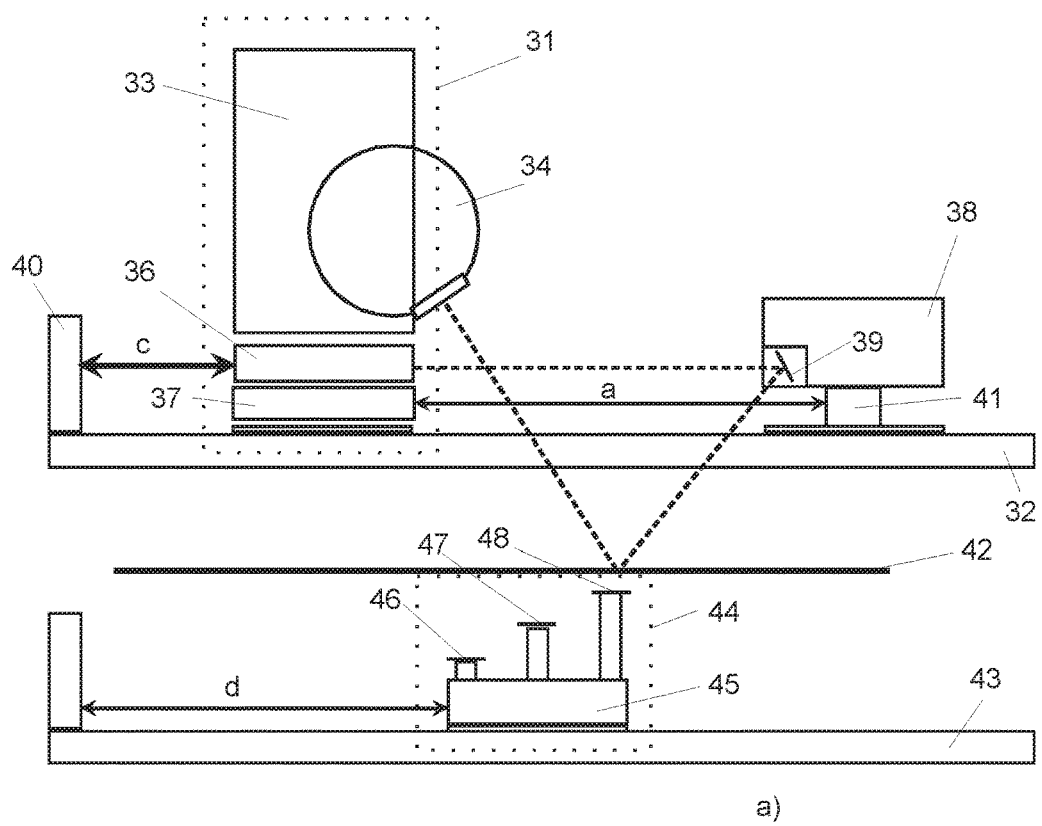
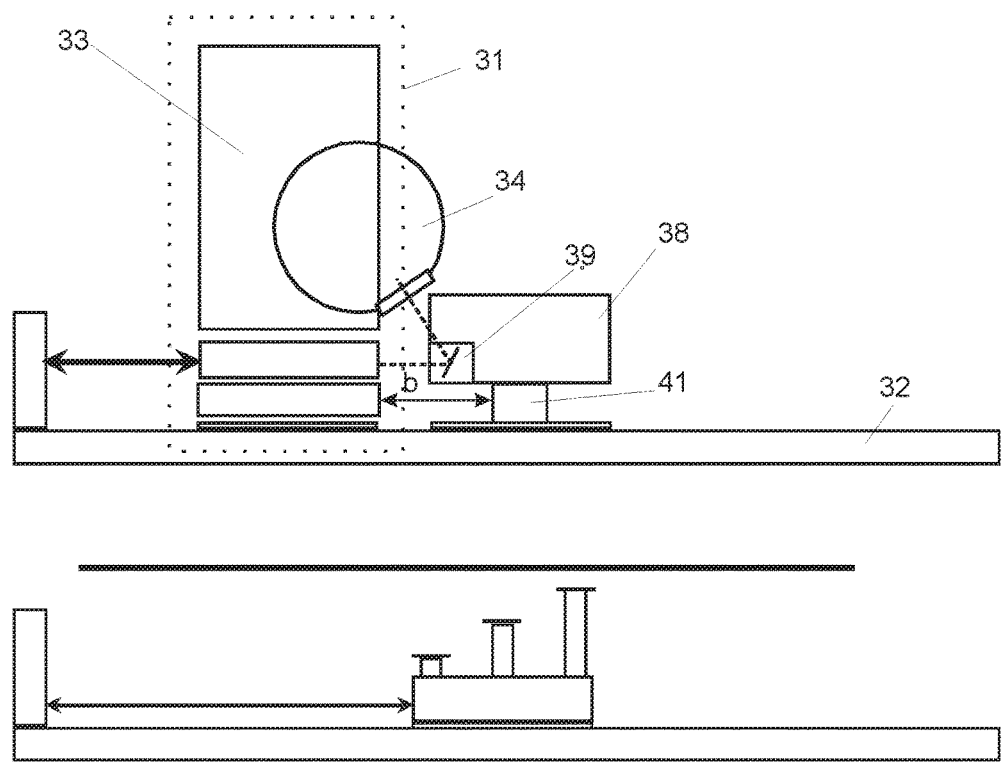
Fig. 4

MEASURING ARRANGEMENT FOR REFLECTION MEASUREMENT

The invention relates to a measuring arrangement for reflection measurement having the features of the preamble of claim 1.

Measuring arrangements of the generic type are used for example for the spectrometric examination of surfaces in order to determine properties such as color and/or luster of the surface.

The color measurement is often carried out by means of a reflection measurement.

The measurement of reflectivity of any sample can be realized either by means of a relative measurement against a known reflection standard assumed to be invariable over time, or by means of an absolute measurement with the use of a suitable beam path.

For color measurement using standards, three internationally standardized measurement geometries are known, for example, which are characterized by the angles at which the sample is illuminated and observed. At 45°/0°, the illumination is carried out at an angle of 45° and the observation is carried out at 0°. At 0°/d, the illumination is carried out at 0° (normal), and the light that is diffusely reflected via a photometer sphere (Ulbricht sphere) is measured at a location. At d/8° or d/0°, illumination is carried out diffusely via a photometer sphere and the light reflected back from the sample is measured at 8° or 0°, respectively.

The individual color impression at different observation angles than the standardized observation angles may deviate greatly here from the standardized color measurement, under certain circumstances. Particularly in the case of reflective and/or specially coated surfaces, considerable deviations in color perception may arise here, depending on the viewing angle.

DE 699 20 581 T2 discloses a multi-channel measuring head which, with a d/8° measurement geometry, enables a combined measurement of color and surface effects with a relative measurement.

DE 60 2005 005 919 T2 describes a portable goniometric spectrometer whose optical system provides different measurement angles along an illumination reference channel by means of a plurality of illumination sources. A shutter mechanism here comprises an internal reference for measuring the reference parameters with a closed opening. A measurement interface is directly connected to the sample to be measured via contact elements, in order to define a sample plane perpendicular to the measurement axis.

DE 20 2012 010 549 U1 discloses an autonomous handheld measuring device with relative measurement which comprises a plurality of illumination sources that directs directional illumination light onto a measurement window at different angles. The reflected light is processed by different spectral and imaging receivers arranged in the measuring device.

US 2005/015185 A1 describes a device for measuring absolute reflection spectra for which a pivotable mirror is arranged between sample and detector in the measurement beam path. In the case of the measurement without a sample, the detector has to be moved in a complex fashion.

The absolutely directional reflection can be measured by the use of compensation methods such as the VW or VN arrangement. The different solution approaches here always ensure that the transfer function for the reference measurement and the measurement at the sample differs only in the reflectivity of the sample.

Particularly for the accurate absolute measurement of highly reflective samples, the VW configuration has proved to be worthwhile, in which the light is reflected twice at the sample and the square of the reflection can accordingly be measured directly. Corresponding measurement inserts are available for some spectrometers.

The disadvantage of the VW or VN arrangements is primarily that, for switching between sample measurement and reference measurement, the mirror has to be swung into two different planes between which the sample plane is arranged. Such arrangements are designed for laboratory use.

DE 10 2012 208 248 B3 describes an optical waveguide-based color sensor system that performs absolute measurement with compensation of a change in distance of the sample. In this case, an illumination channel, a photosensitive secondary reception channel and a photosensitive main reception channel are used in a tripartite fiber bundle. The reception channels have different characteristic functions with respect to the distance sensitivity.

DE 199 50 588 B4 discloses an apparatus and a method for quality control of, in particular, lacquered or varnished goniochromatic surfaces. One or more of the characteristic variables color, luster, haze or others are determined. For this purpose, two light sources and an optical system and filter device are arranged in a housing in such a way that the spectrally predetermined light impinges on the sample window at an angle of 45°. The reflected light is received via a light capture device of an optical waveguide and is directed to a measuring device. A plurality of such measuring devices can be directed at the sample window at different angles.

In industrial applications, a variable sample location often proves to be problematic for the absolute color measurement. In such applications, a distance variation of the sample is compensated for e.g. by means of an overexposure of the sample (larger light spot diameter) or distance sensors or position-sensitive light detectors are additionally used to compensate for the measurement errors.

The object of the invention is to provide a robust measuring arrangement for absolute reflection measurement on a sample which is suitable in particular for inline measurement in the process for producing large coated surfaces such as, for example, glass panes, films or other sheetlike or large-area materials.

The object is achieved by means of a measuring arrangement having the features of claim 1.

A measuring arrangement according to the invention for detecting an absolute reflection spectrum of a sample firstly comprises, in a known manner, a light source for generating measurement light, a homogenizer for generating a uniform spatial illuminance distribution of the measurement light, a movable reflector and a receiver. The reflector guides the measurement light emitted by the light source and/or the light reflected from the sample to the receiver. The receiver, in a known manner, can be connected to a spectrometer or else directly form the input of a spectrometer. For the purposes of an absolute reflection measurement, the reflector both for a reference measurement and for a sample measurement is positioned in an observation beam path.

According to the invention, the reflector both in the measurement position and in the reference position is arranged on the same side of the sample as the light source in order to feed the measurement light to the receiver.

The measurement of the absolute reflection is characterized in that it is carried out without the aid of a known sample.

In order to evaluate the absolute reflection, either the light source or the measurement light can be spectrally tunable (monochromator) or/and the receiver can spectrally analyze the light (spectrometer).

Furthermore it is possible to vary the polarization properties of the measurement light upstream and/or downstream of the sample by means of polarizer/analyzer.

Preferably, the homogenizer is a hollow body (e.g. Ulbricht sphere or Ulbricht tube or freely fashioned sphere-cylinder structure) which is diffusely reflective at its inner surface and which also comprises the light source, with a light exit opening through which the measurement light passes to the sample. In the diffusely reflective hollow body, at every point the same radiation intensity is generated in every direction, such that almost arbitrary illumination and/or observation angles can be realized depending on the setting up of the observation beam path in a specific region.

The reflector is a plane mirror in the simplest case, but can also be an imaging mirror in modified embodiments for specific applications. It goes without saying that a plurality of reflectors can also be used.

The receiver is preferably embodied as an optical waveguide bundle with an input optical system, but in modified embodiments can also be an individual optical waveguide with or without an input optical system, an entrance opening of a free space optical system or an entrance opening of a spectrometer. The receiver or an element disposed downstream thereof converts the measurement light coming from the sample or the reflector into an electrical signal, which is processed further in a known manner.

Both during the reference measurement and during the sample measurement, the light passes through all transmissive or reflective parts of the measuring structure and angles of incidence and reflection do not change their absolute value in the process.

The advantages of the invention can be seen, in particular, in the fact that a very inexpensive and robust measuring arrangement that is insensitive to a change in position of the sample can be realized for large-area samples (e.g. in the coating of large-area industrial glasses or films). No part of the measuring structure need to be moved in or through the sample plane and the sample need not to be removed from the sample plane for reference measurements.

In preferred embodiments, components of the measuring arrangement are placeable in a traverse arrangement and positionable there.

In the absolute measurement, firstly for referencing purposes, the measurement light emitted by the light source is directed via a reflector to a receiver and the intensity of the received measurement light is determined. If a sample is then introduced into the beam path and the (wavelength-dependent) intensity of the measurement light is determined again, the spectral characteristic of the measured sample can be determined from the ratio of the two (wavelength-dependent) measurement signals. The principle of absolute measurement is known to the person skilled in the art; therefore, a detailed explanation is dispensed with here.

Advantageously, the measuring arrangement can be used for detecting the reflection spectra at different observation angles.

The reflector is preferably positionable in a first measurement position and a first reference position. In this case, in both first positions, an illumination angle and an observation angle are set to be equal in magnitude.

Advantageously, the reflector is additionally positionable in a second and, if appropriate, further measurement and reference positions, such that different illumination and observation angles are settable. It is thus possible to identify desired or undesired differences at different viewing angles.

A first variant of the particularly preferred embodiment having a very simple and robust structure is suitable for measuring specular samples. In this case, the reflector and the receiver are arranged in a receiving plane which extends substantially between the light source and the sample parallel to a sample plane. Advantageously, the reflector in this case (otherwise in the case of a VW measuring arrangement) need not be swung from a plane situated below the sample into a plane situated above the sample, but rather can be positioned within the receiving plane. As a result, the structure becomes compact and the actuating mechanism for the reflector becomes produceable in a simple and cost-effective manner.

With a simple pivoting mechanism for the reflector, the latter can be positioned from the first reference position into the first measurement position for a specific illumination angle.

If the illumination and/or observation angles are intended to be varied, this can be realized for example with a drive in a linear guide and a rotating and/or tilting mechanism for the reflector. In this case, the linear guide is preferably aligned substantially parallel to the sample plane. The different angles of the observation beam paths can be set solely by means of the position and inclination of the reflector.

A second variant of the particularly preferred embodiment is suitable for measuring diffusely and specularly reflective samples. In this variant, the reflector and the receiver are arranged within the hollow body. In this case, the light exit opening also serves as a measurement window through which the reflected measurement light is directed via the reflector to the receiver. An illumination and observation angle is set depending on the inclination of the reflector.

The light exit opening is preferably embodied as an elongate hole and thereby allows the positioning of a circular measurement spot over a range of different measurement angles. Further aspects in the advantageous configuration of the light exit opening are described in DE 10 2013 219 830 and included within their full scope in this application.

The further processing of the reflection data is carried out in a known manner by means of a spectrometer to which the measurement light arriving in the receiver is communicated.

Advantageously, transmission and back-surface reflection properties of the sample can also be determined by means of an additional module to be arranged below the sample plane.

Figure 6:
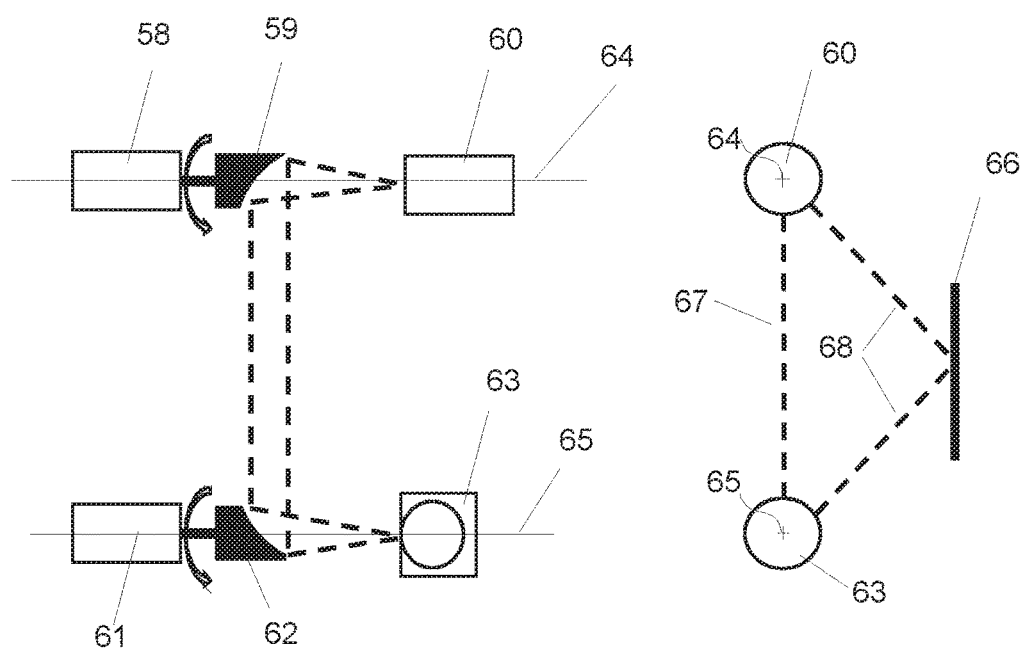
Figure 7:
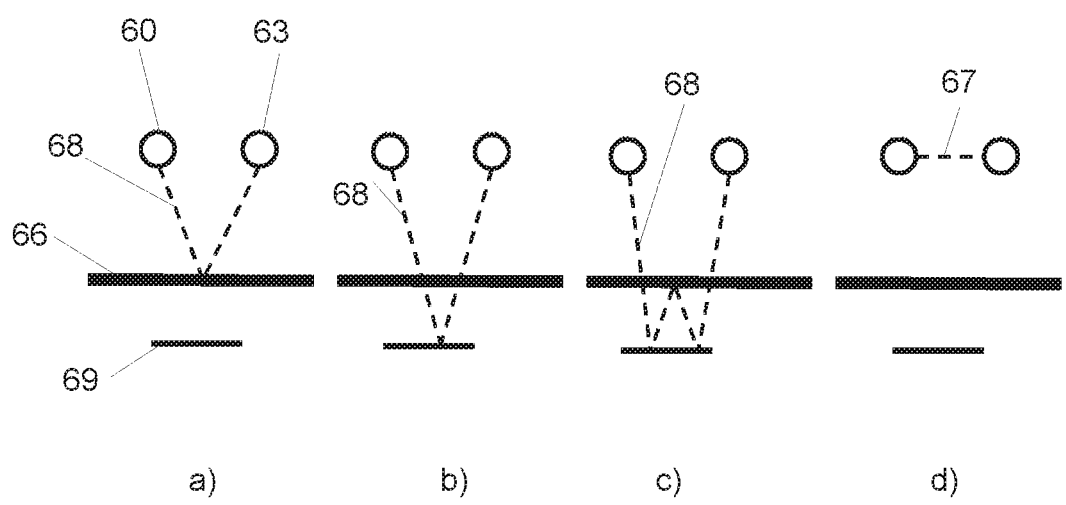

Some preferred configurations of the invention are explained in greater detail below with reference to the figures. In the figures:

FIG. 1: shows a first preferred embodiment of the invention for measuring specular samples in a basic illustration with a setting of a first illumination angle;

FIG. 2: shows the embodiment shown in FIG. 1 with setting of a second illumination angle;

FIG. 3: shows a second preferred embodiment of the invention for measuring specular samples with a fixed illumination angle;

FIG. 4: shows a third preferred embodiment for measuring specular samples in a modular design;

FIG. 5: shows a fourth preferred embodiment of the invention for measuring diffuse and specular samples in a basic illustration;

FIG. 6: shows a fifth preferred embodiment of the invention having two rotatable reflectors;

FIG. 7: shows possible measurement variants with the embodiment illustrated in FIG. 6.

FIGS. 1 and 2 show basic schematic diagrams of a first preferred embodiment of the invention with a setting of different illumination angles α. In this case, an illumination angle $α_1$ of 8° is set in FIG. 1, while FIG. 2 shows a set illumination angle $α_2$ of 45°. In this case, illustration a) shows settings for a reference measurement and illustration b) shows settings for a sample measurement. In sequential measurements, illumination angles of 0° to 65° are settable and measurable with this arrangement.

An Ulbricht sphere 01 having a diffusely reflective inner surface 02 comprises a light source (not illustrated) and a light exit opening 03. The advantage of the use of the Ulbricht sphere 01 is that at every point of the inner surface 02 the same light intensity is reflected in every direction and hence every illumination direction can be generated in a simple manner, provided that the light exit opening 03 is correspondingly dimensioned.

A sample 04 is arranged at a distance from the Ulbricht sphere 01 in a sample plane 05. In this case, the sample 04 is a large-area sample such as, for example, industrial glass or film or the like. A reflector 06 and a receiver 07 are arranged in a plane 08 moving substantially parallel to the sample plane 05. The reflector 06 is arranged adjustably in terms of its inclination and displaceably in the plane 08. Proceeding from the receiver 07, an observation beam path 09 is illustrated, which, as viewed from the Ulbricht sphere 01, also constitutes an illumination beam path.

In illustrations a), the reflector 06 in each case for a reference measurement is set with regard to its position and inclination such that a specific angle of incidence of the illumination beam path 09 is reflected and directed to the receiver 07.

In illustrations b), the reflector 06 is in each case displaced in the plane 08 and altered in terms of its inclination such that an illumination angle $α_1$, $α_2$ corresponding to illustration a) is also set on the sample 04.

FIG. 3 shows a second preferred embodiment of the invention, in which a fixed illumination angle or observation angle is set in a simple manner. This embodiment is particularly suitable for integrating into a fixed production environment if only the measurement at a specific angle is required. In this embodiment, a measuring arrangement 11 comprises an illumination unit 12 having an Ulbricht sphere 13. The Ulbricht sphere 13 has a light exit opening 14. The measuring arrangement 11 furthermore comprises a reflector 16 arranged on a pivoting arm 17. The pivoting arm 17 is pivotable from a measurement position 18 into a reference position 19 (illustrated in a dashed fashion) by means of a rotary drive (not illustrated). A sample 21 is guided past the measuring arrangement 11 at a distance therefrom or is positioned in front of the latter, such that measurement light emerging from the light exit opening 14 at an illumination angle of $α_3=55°$ impinges on the sample 21 as a measurement spot, and is guided by the latter via the reflector 16 situated in the measurement position 18 to a receiver 22. In this case, the inclination and the distance of the reflector 18 with respect to the receiver 22 are advantageously set simultaneously by means of a pivoting movement of the pivoting arm 17. A pivoting angle β of the pivoting arm 17 is set such that the same illumination angle $α_3$ relative to a sample plane is produced both in the measurement position 18 and in the reference position 19. In this embodiment, the receiver is fed to a spectrometer for evaluation purposes with the aid of an optical waveguide 23.

FIG. 4 shows a third embodiment of the invention in a modular design, said embodiment being particularly suitable for crossbar applications. This form is particularly suitable for application for the direct monitoring of the material properties in a process for producing sheetlike materials or materials which are transported along a path in the process (e.g. by means of a conveyor belt). These might be for example film coating installations, production rails of large glass panes or the like. In this case, illustration a) shows a measurement position and illustration b) shows a reference position. This embodiment advantageously allows an automated measurement/scanning of a sample location at freely selectable observation angles (0 to 65°). Standard-conforming and non-standardized measuring arrangements are thus realizable with one measuring arrangement.

The measuring arrangement comprises a first module 31, which is arranged in a first linear guide 32 and comprises an illumination unit 33 having an Ulbricht sphere 34 and a receiver module 36 arranged below the illumination module 34. The first module 31 furthermore comprises a drive 37.

In the first linear guide 32, provision is furthermore made of a reflector module 38 having a reflector 39 and having a dedicated drive 41 for the linear adjustment of the reflector module 38 in a receiving plane. In specific embodiments, via a gear mechanism or similar mechanism, said drive 41 can simultaneously serve for the tilting and/or rotational adjustment of the reflector 39. The first linear guide 32 is advantageously integrated into a crossbar arrangement and arranged above a sample 42 which is to be examined and which is situated in the production process. The first module 31 and the reflector module 38 as parts of the measuring arrangement according to the invention are positioned at a distance a with respect to one another and the reflector 39 is swung in the direction of sample 42, such that a measurement position for measuring a 45° illumination/observation is set (illustration a). The illumination/observation beam path is illustrated in a dotted fashion. Sequentially different illumination angles are then settable by variation of the distance a and the position of the reflector 39. It goes without saying that a distance c between the first module and a zero position 40 can also be implemented for the distance change. The distances can be measured by means of scales with absolute encoding, for example, as is customary in the case of such crossbar systems.

In illustration b), as a result of the tilting of the reflector 39 and the setting of a distance b between first module 31 and reflector module 38, a reference position for a 45° measurement is illustrated. The reference measurement can be carried out at any time and can be buffer-stored in an apparatus controller.

Below the sample 42, in a second linear guide 43, provision is made of a third additional module 44 having a dedicated drive 45, with which a rear-side reflection measurement and transmission measurement are furthermore possible. For this purpose, here three reflectors 46, 47, 48 are arranged at different levels. With a corresponding positioning of the additional module by means of a distance d, this sets whether the light transmitted by the sample 43 is not fed to the receiver (reflector 46 below the impinging measurement light), is fed to the receiver (reflector 47 below the impinging measurement light) or is fed to the receiver together with light reflected back from the underside of the sample 43. In this regard, depending on the setting of the distance d, the receiver signal consists only of the reflection of the top side, the reflection of the top side plus the light transmitted twice, or the reflection of the top side, the light transmitted twice plus the multiple reflection between the underside of the sample 43 and the mirror 48.

In alternative embodiments, the additional module 44 can also comprise only a single reflector, which is positionable in terms of height for the corresponding measurement purpose. The reflection values of the mirrors must be known and are determined with the aid of the measuring arrangement itself. A further embodiment of the transmission measurement is found in FIG. 6.

Sequential measurements of the reflection up to illumination angles of 75° are possible with a minimum possible number of linear guides and drives. In addition, rear-side reflection and transmission measurements can be carried out in a known manner.

FIG. 5 shows a fourth preferred embodiment of the invention in a basic schematic diagram. In this embodiment, a reflector 52 and a receiver 53 are arranged within an Ulbricht sphere 51. A sample 54 is illuminated through a light exit opening 56. In order to cover a large angular range of illumination directions, the light exit opening 56 has an optimized shape. The light exit opening 56 has a stop 57 which, besides the reflector tilting, enables a size of the illumination window 56 coordinated with the desired illumination angle. The receiver 53 is tilted out laterally from the perpendicular central plane of the sphere to an extent such that the sphere meridian opposite the reflector 52 is available as a measurement light source in a completely undisturbed manner, e.g. by approximately 20°. The reflector 52 is accordingly tilted laterally by half the angle. See illustration (f) in plan view.

Illustration a) shows the illumination of the sample 54 at an illumination and observation angle of 8°, illustration c) of 45° and illustration e) of 60°. Illustrations b) and d) show the reference measurement settings of the reflector 52 for illumination angles of 8° or 45°, respectively.

Illustration f) shows a plan view of the Ulbricht sphere 51. The particular shape of the light exit opening 56 and the inclination of the receiver 53 are discernible in this illustration. Since it is the aim of this arrangement, too, for the measurement light to originate from the same area of the light source (Ulbricht sphere) for all measurement angles both in the reference measurement (directly) and in the sample measurement (via the sample).

FIG. 6 shows a fifth preferred embodiment of the invention in illustration a) in a plan view and in illustration b) in a side view. The measuring arrangement comprises two imaging off-axis mirrors 59, 62, which are rotatable about an optical axis of a light source 63 and of a receiver 60 and thereby deflect the beam path. In this case, the optical axes 64, 65 of receiver 60 and light source 63 are aligned parallel to a plane in which a sample 66 is arranged.

If the receiver 60, which may be a free space spectrometer, for example, is aligned in the direction of the light source 63 by means of a drive 58 of the imaging off-axis mirror 59, and if the light source 63 is aligned with the receiver 60 by means of a drive 61 of the off-axis mirror 62 (beam path 67, illustration b)), a reference measurement can be carried out which determines the intensity of the light source 63 depending on the apparatus function.

If receiver 60 and light source 63 are aligned with a sample 66 at a suitable angle (beam path 68, illustration b)), then the intensity of the light source 63 can be measured depending on the apparatus function and the reflection of the sample 66.

The sample reflection as the variable sought can then be calculated in a simple manner from the quotient of sample measurement and reference measurement. The intensity of the light source 63 and the dependence of the apparatus function cancel each other out in the quotient and are thus omitted as unknown variables. The principle of an absolute measurement is thus realized. The observation angle γ with respect to the sample 66 can be varied by means of the distance from receiver 60 to light source 63 or by means of the distance from receiver 60 and light source 63 to the sample 66.

FIG. 7 shows the variants of the reflection and transmission measurement with respect to the embodiment shown in FIG. 6. As already described in FIG. 4, by using a mirror 69 on the rear side of the sample 66 and suitably varying the angular position of the mirrors 59 and 62, besides reflection (FIG. 7a) it is also possible to determine the transmission (FIG. 7b) and the reflection of the sample 66 from the rear side (FIG. 7c). The reference measurement (FIG. 7d) can be carried out in the presence of the sample 66, which constitutes a considerable advantage in the production process. The reflection properties of the mirror 69 must be known and can be updated regularly e.g. during maintenance by means of the measuring arrangement itself.

| List of reference signs | |
|---|---|
| 01 | Ulbricht sphere |
| 02 | Inner surface |
| 03 | Light exit opening |
| 04 | Sample |
| 05 | Sample plane |
| 06 | Reflector |
| 07 | Receiver |
| 08 | Plane |
| 09 | Observation beam path |
| 10 | — |
| 11 | Measuring arrangement |
| 12 | Illumination unit |
| 13 | Ulbricht sphere |
| 14 | Light exit opening |
| 15 | — |
| 16 | Reflector |
| 17 | Pivoting arm |
| 18 | Measurement position |
| 19 | Reference position |
| 20 | — |
| 21 | Sample |
| 22 | Receiver |
| 23 | Optical waveguide |
| 31 | Module, first |
| 32 | Linear guide |
| 33 | Illumination module |
| 34 | Ulbricht sphere |
| 35 | — |
| 36 | Receiver modules |
| 37 | Drive |
| 38 | Reflector module |
| 39 | Reflector |
| 40 | — |
| 41 | Drive |
| 42 | Sample |
| 43 | Linear guide |
| 44 | Additional module |
| 45 | Drive |
| 46 | Reflector |
| 47 | Reflector |
| 48 | Reflector |
| 51 | Ulbricht sphere |
| 52 | Reflector |
| 53 | Receiver |
| 54 | Sample |
| 55 | — |
| 56 | Light exit opening |
| 57 | Stop |
| 58 | Drive |
| 59 | Off-axis mirror |
| 60 | Receiver |
| 61 | Drive |
| 62 | Off-axis mirror |
| 63 | Light source |
| 64 | Optical axis |
| 65 | Optical axis |

-continued

| List of reference signs | |
|---|---|
| 66 | Sample |
| 67 | Beam path |
| 68 | Beam path |
| 69 | Mirror |

The invention claimed is:

1. A measuring arrangement for detecting an absolute reflection spectrum of a sample in a process for producing the sample, comprising:
 a light source for generating measurement light;
 a homogenizer comprising a single light exit opening for generating a uniform spatial illuminance distribution of the measurement light;
 a movable reflector; and
 a receiver for collecting the measurement light reflected from the sample and/or the reflector,
 wherein the reflector both for a reference measurement and for a sample measurement is positioned in an observation beam path and arranged on the same side of the sample as the light source in order to feed the reflected measurement light to the receiver.

2. The measuring arrangement as claimed in claim 1, wherein the homogenizer is a hollow body which is diffusely reflective at its inner surface and which comprises the light source.

3. The measuring arrangement as claimed in claim 1, wherein the reflector is positionable in a first measurement position and a first reference position, wherein in each case the same illumination angle and observation angle are set.

4. The measuring arrangement as claimed in claim 3, wherein the reflector is positionable at least one second defined measurement position in order to vary the observation beam path with regard to the illumination angle and the observation angle, wherein with respect to the second measurement position a second defined reference position of the reflector is determined, into which the reflector is positionable.

5. The measuring arrangement as claimed in claim 1, wherein the reflector and the receiver are arranged in a receiving plane (08) which extends substantially between the light source and the sample parallel to a sample plane.

6. The measuring arrangement as claimed in claim 5, wherein the first measurement position and the first reference position are situated in the receiving plane.

7. The measuring arrangement as claimed in claim 5, wherein the reflector is movable from the first measurement position into the first reference position by means of a pivoting drive.

8. The measuring arrangement as claimed in claim 5, wherein the reflector is arranged in a linear guide and is positionable into different measurement positions and reference positions by means of a linear drive and a rotating or tilting mechanism within the receiving plane.

9. The measuring arrangement as claimed in claim 2, wherein the reflector and the receiver are arranged within the hollow body.

10. The measuring arrangement as claimed in claim 9, wherein the reflector is positionable by means of a rotating or tilting mechanism.

11. The measuring head as claimed in claim 2, wherein the light exit opening is in the form of an elongate hole.

* * * * *

UNITED STATES PATENT AND TRADEMARK OFFICE
CERTIFICATE OF CORRECTION

PATENT NO. : 10,054,484 B2  
APPLICATION NO. : 15/328523  
DATED : August 21, 2018  
INVENTOR(S) : Jörg Margraf et al.

Page 1 of 1

It is certified that error appears in the above-identified patent and that said Letters Patent is hereby corrected as shown below:

On the Title Page

Column 1, item (71), "Applicant: Carl Zeiss Spectroscopy GmgH, Jena (DE)", should read
--Applicant: Carl Zeiss Spectroscopy GmbH, Jena (DE)--

Signed and Sealed this
Twenty-second Day of September, 2020

Andrei Iancu
*Director of the United States Patent and Trademark Office*